(12) United States Patent
Kim et al.

(10) Patent No.: US 7,295,001 B2
(45) Date of Patent: Nov. 13, 2007

(54) MAGNETOSTRICTIVE TRANSDUCER USING TAILED PATCHES AND APPARATUS FOR MEASURING ELASTIC WAVE USING THE MAGNETOSTRICTIVE TRANSDUCER

(75) Inventors: Yoon-young Kim, Seoul (KR); Chan-il Park, Gunpo-si (KR); Seung-hyun Cho, Ansan-si (KR); Woo-chul Kim, Suwon-si (KR)

(73) Assignee: Seoul National University Industry Foundation, Seoul (KR)

( * ) Notice: Subject to any disclaimer, the term of this patent is extended or adjusted under 35 U.S.C. 154(b) by 218 days.

(21) Appl. No.: 11/092,976

(22) Filed: Mar. 30, 2005

(65) Prior Publication Data

US 2006/0145692 A1    Jul. 6, 2006

(30) Foreign Application Priority Data

Dec. 31, 2004    (KR)    ............... 10-2004-0118017

(51) Int. Cl.
*G01B 7/24*    (2006.01)
*G01L 3/00*    (2006.01)
(52) U.S. Cl. ................... 324/209; 73/862.335
(58) Field of Classification Search ................ 324/209; 73/862.333–862.336
See application file for complete search history.

(56) References Cited

U.S. PATENT DOCUMENTS

| | | | | |
|---|---|---|---|---|
| 4,823,617 A | * | 4/1989 | Hase et al. | ............ 73/862.335 |
| 4,852,411 A | * | 8/1989 | Beihoff | .................. 73/862.335 |
| 5,193,267 A | * | 3/1993 | Satoh et al. | .................. 29/606 |
| 5,386,733 A | * | 2/1995 | Hesthamar et al. | .... 73/862.333 |
| 2002/0189372 A1 | * | 12/2002 | Wallin et al. | .......... 73/862.333 |
| 2005/0179430 A1 | * | 8/2005 | Park et al. | .................. 324/240 |

FOREIGN PATENT DOCUMENTS

| JP | 2004-535936 | * | 7/1994 |
|---|---|---|---|
| JP | 1997-516474 | * | 3/1997 |

* cited by examiner

*Primary Examiner*—Edward Lefkowitz
*Assistant Examiner*—Kenneth J Whittington
(74) *Attorney, Agent, or Firm*—Sughrue Mion, PLLC

(57) ABSTRACT

A magnetostrictive transducer generating a torsional wave in a subject having a predetermined section and measuring a torsional wave propagating in the subject. In the magnetostrictive transducer having a ferromagnetic patch attached to a predetermined position of a subject, a cylindrical insulator installed around the periphery of the ferromagnetic patch, and a coil wound around the cylindrical surface of the insulator, a torsional wave is generated based on a magnetostrictive effect to then be induced to the subject when current is applied to the coil. The ferromagnetic patch includes a strip unit attached to the subject in an inclined manner with respect to an axial direction of the subject and transferring the torsional wave to the subject; and tail units formed at opposite ends of the strip unit and concentrating a magnetic flux on the strip unit when current is applied to the coil.

9 Claims, 12 Drawing Sheets

MAGNETOSTRICTIVE TRANSDUCER USING TAILED PATCHES AND APPARATUS FOR MEASURING ELASTIC WAVE USING THE MAGNETOSTRICTIVE TRANSDUCER

This application claims priority from Korean Patent Application No. 10-2004-0118017 filed on Dec. 31, 2004 in the Korean Intellectual Property Office, the disclosure of which is incorporated herein by reference in its entirety.

BACKGROUND OF THE INVENTION

1. Field of the Invention

The present invention relates to a magnetostrictive transducer for generating a torsional wave in a subject using magnetostriction effect, and more particularly, to an apparatus for both generating a torsional wave in a subject such as a shaft or a beam having a predetermined cross section and measuring the torsional wave propagating in the subject.

2. Description of the Related Art

Magnetostriction refers to the mechanical strain that occurs in ferromagnetic materials when they are subjected to a magnetic field. It is also referred to as the Joule effect. Conversely, an inverse magnetostrictive effect refers to the change in magnetization of ferromagnetic materials when subject to mechanical stress, which is also referred to as the Villari effect.

Since transducers that exploit magnetostriction can measure a strain in a subject without being in contact with the subject, they have been applied to various fields that cannot use contact sensors. The use of magnetostriction makes it possible not only to generate elastic ultrasonic waves in a non-contact manner but also to generate ultrasonic waves having larger amplitude than that of ultrasonic waves generated by conventional techniques that use the piezoelectric effect. Ultrasonic waves that can be generated from a waveguide body, e.g., a rod or a piping member, include longitudinal, transverse, and torsional waves.

In the first mode of the torsional waves, little dispersion occurs. Dispersion indicates a velocity variation depending on frequency. Thus, the first mode of the torsional wave can be effective in evaluating the structural characteristics of a rod or a piping member.

In general, ferromagnets include substances such as iron, nickel, and cobalt. Among these ferromagnets, nickel is used in an embodiment of the invention as it is a soft magnetic material characterized by having a sharply rising magnetization curve and small hysteresis and returning to its original shape after removal of a magnetic field.

Figure 1:
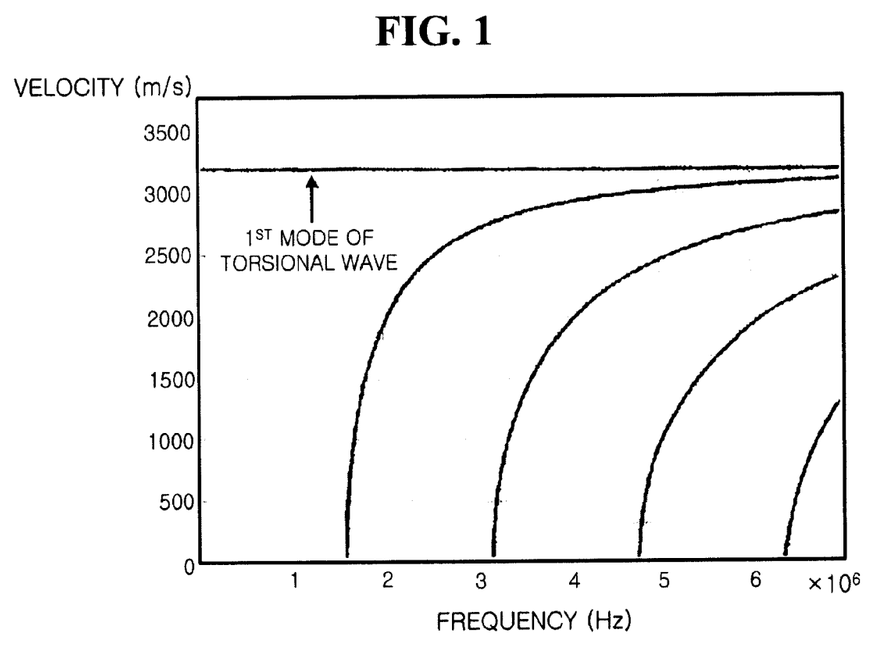
FIG. 1 shows group velocity curves with respect to frequencies in a torsional wave that are propagated through a rod member.

FIG. 1 shows group velocity curves with respect to frequencies in a torsional wave propagating in a rod member. The rod member is an aluminum pipe having a thickness (t) of 1 mm, an outer diameter (d0) of 25 mm, a density ($\rho$) of 2800 kg/m$^3$, and an elastic coefficient (E) of 73 GPa.

As shown in FIG. 1, dispersion hardly ever occurs in the first mode among the group velocity curves. Thus, for example, in remote detection, if a non-destructive testing is carried out using a torsional wave, it is be very helpful in detecting defects of a pipe or the like as it maintains its form upon reflection.

Figure 2:
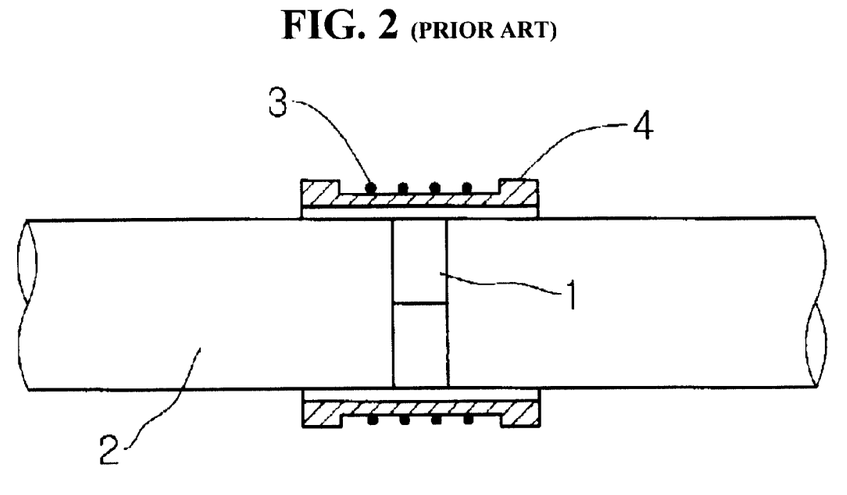
FIG. 2 illustrates an example of a conventional magnetostrictive transducer.

As shown in FIG. 2, a conventional magnetostrictive transducer includes a thin nickel strip 1 that is wound around a subject 2, an insulator 4 installed around the nickel strip 1, and a coil 3 wound around the insulator 4.

When a defect of the subject 2 is scanned using the conventional magnetostrictive transducer, the nickel strip 1 is wound around and attached to the cylindrical surface of a pipe, and is magnetized in the circumferential direction of the strip 1 using a permanent magnet (not shown). An elastic wave is generated by applying a magnetic field to the coil 3 around the magnetized nickel strip 1 and this generated elastic wave is measured. When the magnetic field is applied to the nickel strip 1, a torsional wave is generated in the subject 2. The generated torsional wave propagates along the subject 2 and is reflected back from an end of the rod member on an area having a structural defect. Then, the magnetic field of the nickel strip 1 is changed by the reflected torsional wave.

Figure 3A:
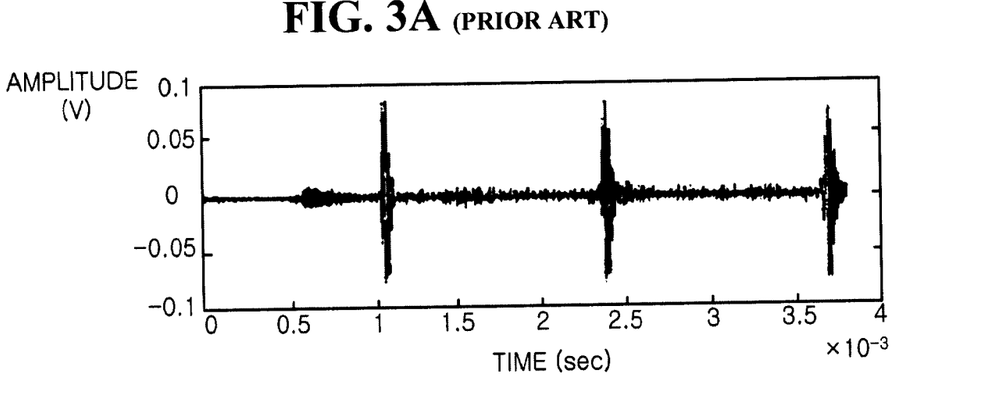
FIGS. 3A and 3B are graphs showing signals measured using the conventional magnetostrictive transducer shown in FIG. 2.
Figure 3B:
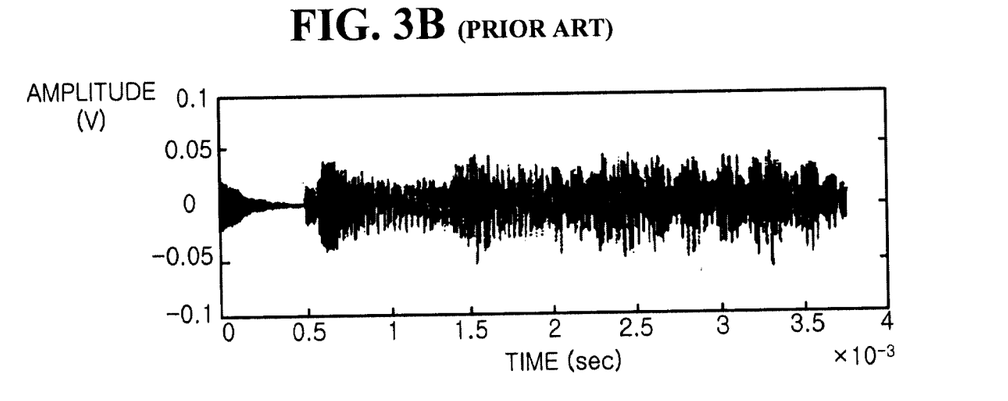

FIGS. 3A and 3B are graphs showing signals measured using a elastic wave (particularly, a torsional wave) generated by the conventional magnetostrictive transducer shown in FIG. 2. An input current to the coil 3 is 3 ampere in FIG. 3A and is 6 ampere in FIG. 3B.

As shown in FIGS. 3A and 3B, since a waveform generated by an input current in the conventional magnetostrictive transducer is very sensitive to magnetic intensity, it is difficult to generate a torsional wave having a large amplitude. As the magnetic intensity of an alternating magnetic field generated in the coil increases, the magnetic intensity of a magnetic field caused by the latent magnetization of the nickel decreases. Thus, as shown in FIG. 3B, a longitudinal wave other than the torsional wave is unintentionally generated resulting in a complex signal and making it difficult to distinguish the torsional wave from other waves.

In other words, if amount of pre-magnetization of the nickel strip 1 in the circumferential direction of the subject 2 and a magnetic intensity along the axis of the coil 3 are not appropriate, the conventional magnetostrictive transducer may generate waves other the a torsional wave. Also, since the nickel strip 1 is a soft magnetic material, it should be pre-magnetized again to be used for an extended period of time.

To overcome such a problem, the inventor of the present invention has proposed a new method as published in a paper entitled "Generation of Induced Torsional Wave and Detection of Defect of Pipe Using Magnetostrictive Transducer" in Transactions of the Korean Society for Noise and Vibration Engineering (Vol. 14, Second Edition, pp. 144-149, 2004; Yoon Young Kim et al.).

Figure 4:
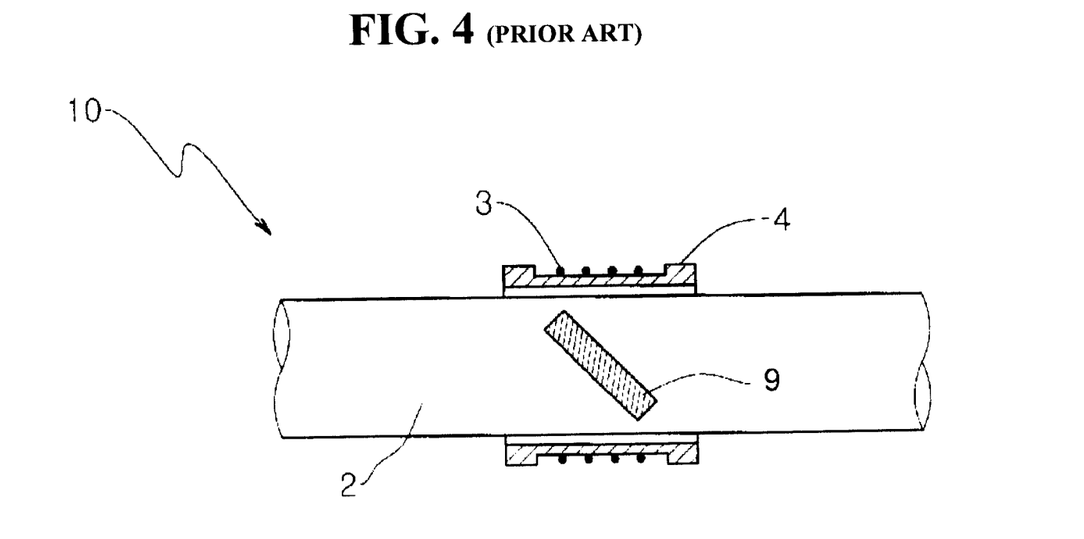
FIG. 4 illustrates an example of a conventional magnetostrictive transducer using a rectangular patch.

According to the method suggested in the above-stated paper, as shown in FIG. 4, a rectangular nickel patch 9 is attached to a subject 2 that is to be scanned at an angle of 45° with respect to the axis direction of the subject 2. The elastic wave generated by attaching the nickel patch 9 in the above-described manner is a torsional wave, unlike in conventional magnetostriction. The generated torsional wave propagates along the subject 2 and is reflected back from the other end or a defective area of the subject 2.

When a current is input to a solenoid coil 3 wound around the nickel patch 9, a magnetic flux is also created at an angle along the nickel patch 9. At the same time, the nickel patch 9 generates a torsional wave mainly by changing the direction of its magnetic field based on magnetostriction. Since a transducer 10 including the nickel patch 9 is able to generate a torsional wave without pre-magnetization or a bias magnetic field, it can be very efficient in generating a torsional wave.

Figure 5A:
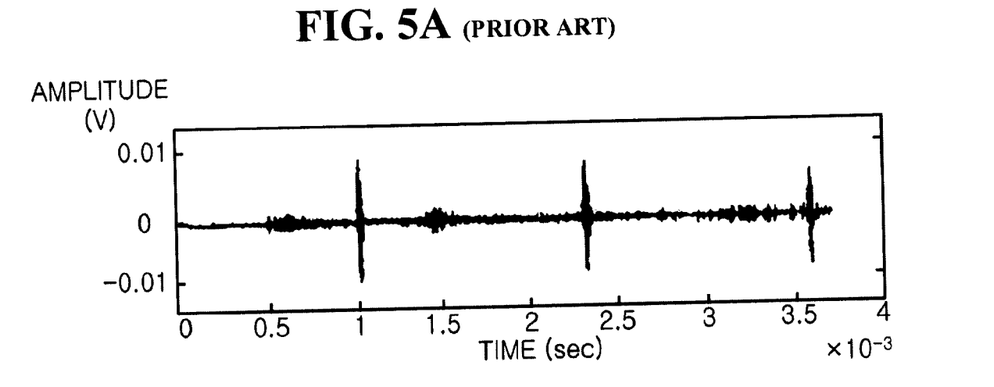
FIGS. 5A and 5B are graphs showing signals measured using the conventional magnetostrictive transducer shown in FIG. 4.
Figure 5B:
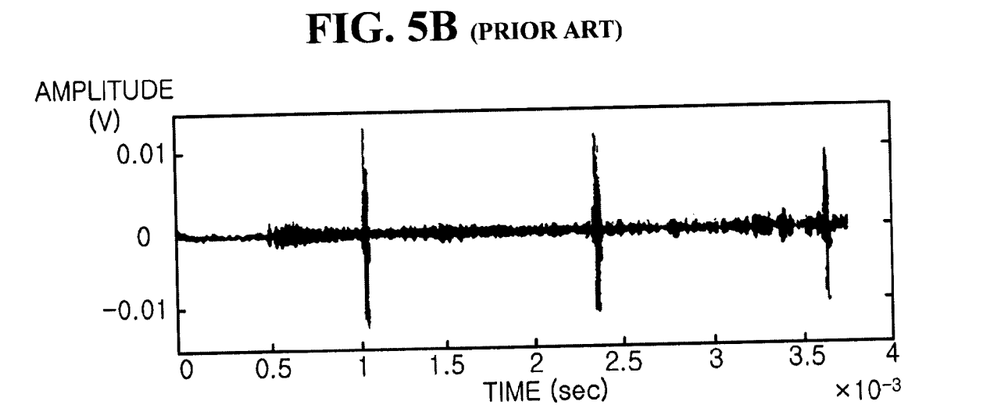

FIGS. 5A and 5B are graphs showing results of experiments carried out using a rectangular patch 9 of 25 mm×3 mm according to the method suggested in the aforementioned paper. In detail, FIG. 5A shows an experimental result when a current of 4.75 ampere is applied to the coil 3 shown in FIG. 4, and FIG. 5B shows an experimental result when a current of 8.44 ampere is applied to the coil 3 shown in FIG. 4. From comparison between the results shown in FIGS. 5A and 5B with those shown in FIGS. 3A and 3B, it can be seen that no other waves than a torsional wave is generated by the method suggested in the aforementioned paper even when an applied voltage is increased. For example, when using the torsional wave to scan for defects, it is possible to accurately detect where the defect is, as confirmed from the fact that there is no distortion in the generated pulse.

While the aforementioned method suggested in the paper has proven to be an efficient method, there is a still need for a transducer capable of generating an output having both a considerable amplitude at a small input signal and a better signal-to-noise ratio.

SUMMARY OF THE INVENTION

The present invention provides a magnetostrictive transducer that concentrates a magnetic flux on a portion of a subject to which stress is applied.

The present invention also provides a magnetostrictive transducer having improved sensitivity and signal-to-noise ratio through concentration of a magnetic flux.

According to an aspect of the present invention, there is provided a magnetostrictive transducer having a ferromagnetic patch attached to a predetermined position of a subject, a cylindrical insulator installed around the periphery of the ferromagnetic patch, and a coil wound around the cylindrical surface of the insulator, wherein a torsional wave is generated based on a magnetostrictive effect to then be induced to the subject when current is applied to the coil, and wherein the ferromagnetic patch includes a strip unit attached to the subject in an inclined manner with respect to an axial direction of the subject and transferring the torsional wave to the subject, and tail units formed at opposite ends of the strip unit and concentrating a magnetic flux on the strip unit when current is applied to the coil.

The ferromagnetic patch may further include a connection unit that is connected to the strip unit and the tail unit and is formed in a direction parallel with the axial direction of the subject.

In addition, a plurality of ferromagnetic patches may be attached to the subject to be spaced a predetermined interval apart from each other in the circumferential direction of the subject.

The subject may be a rod member having a predetermined length.

The magnetostrictive transducer may further include an external insulator that surrounds the coil and the insulator in a manner that it is spaced a predetermined interval apart therefrom, and a bias coil that is wound around the outer surface of the external insulator.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE PREFERRED EMBODIMENT

The present invention will now be described more fully with reference to the accompanying drawings, in which preferred embodiments of this invention are shown. Advantages and features of the present invention and methods of accomplishing the same may be understood more readily by reference to the following detailed description of preferred embodiments and the accompanying drawings. The present invention may, however, be embodied in many different forms and should not be construed as being limited to the embodiments set forth herein. Rather, these embodiments are provided so that this disclosure will be thorough and complete and will fully convey the concept of the invention to those skilled in the art, and the present invention will only be defined by the appended claims. Like reference numerals refer to like elements throughout the specification.

The present invention is directed to a magnetostrictive transducer that generates and measures a torsional wave using a specially designed ferromagnetic patch. The proposed magnetostrictive transducer uses a ferromagnetic patch having a tail (hereinafter, simply referred to as a tailed patch) instead of a rectangular patch that is attached to a subject at a predetermined angle (e.g., 45°) (hereinafter, simply referred to as a rectangular patch).

Since tails of the tailed patch are used to concentrate a magnetic field passing through the tails' surroundings, they are not attached to a subject, but to a central rectangular portion of the tailed patch (hereinafter, referred to as a strip unit), which is attached to the subject as in a conventional rectangular patch. By concentrating the magnetic flux on the central strip unit using the tails, sensitivity of a transducer can be improved. Moreover, a ratio of a magnetostrictive wave to other mode waves, i.e., a signal-to-noise ratio, can be enhanced. It can be seen from the experimental results according to the present invention that a torsional wave can be generated and measured in a very stable and efficient way by employing a transducer having a tailed patch.

Figure 6:
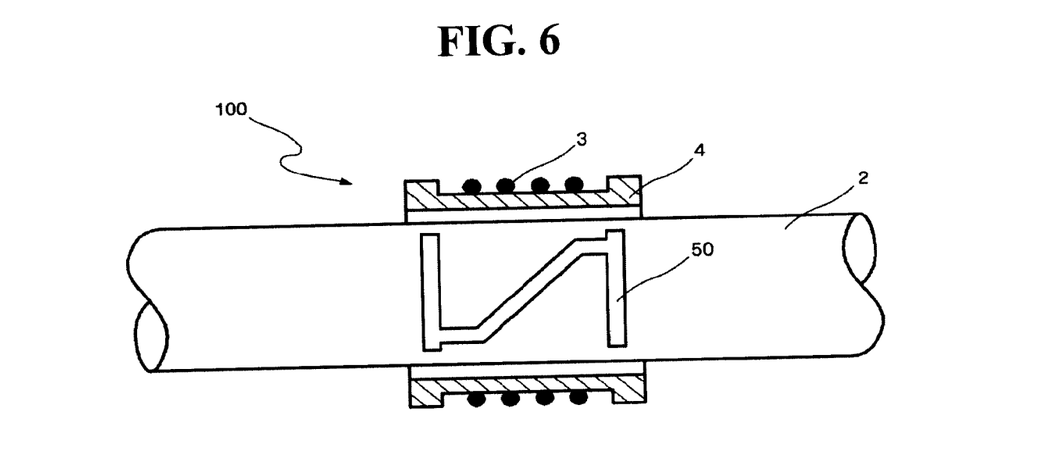
FIG. 6 illustrates the structure of a transducer according to an embodiment of the present invention.

FIG. 6 illustrates the structure of a transducer 100 according to an embodiment of the present invention. The transducer 100 includes a tailed patch 50 whose central strip unit is attached to a face of a subject 2 such as a beam or a rod member, a first insulator 4 that surrounds the tailed patch 50 leaving a predetermined interval therebetween, and a driving coil 3 that is wound around the outer surface of the first insulator 4 and that generates a driving magnetic field when a driving current flows. The tailed patch 50 may be formed of a ferromagnetic material such as iron, nickel, or cobalt.

When a variable current flows through the driving coil 3, a magnetic flux that passes through the inside of the first insulator 4 is generated by magnetic induction. Since the magnetic flux is absorbed by both tails of the tailed patch 50, magnetic flux leakage is reduced compared to the conventional art. The magnetic flux absorbed by the tails flows along the central portion of the tailed patch 50, i.e., the strip unit. When a tailed patch is used the intensity of a magnetic field applied to the strip unit is larger than in a conventional rectangular patch, thus causing large magnetostriction which improves the sensitivity of a transducer.

FIGS. 7A through 7D illustrate forms of a tailed patch having a strip unit inclined at various angles with respect to a subject. To generate a torsional wave, it is preferable that the strip unit be attached to the subject at an angle of 45° with respect to the axis of the subject. However, in the case of an anisotropic subject, it may be desirable to vary the angle. Meanwhile, to generate a typical elastic wave, an angle at which the strip unit is attached to the subject may be appropriately changed according to the specific purpose.

Figure 7A:
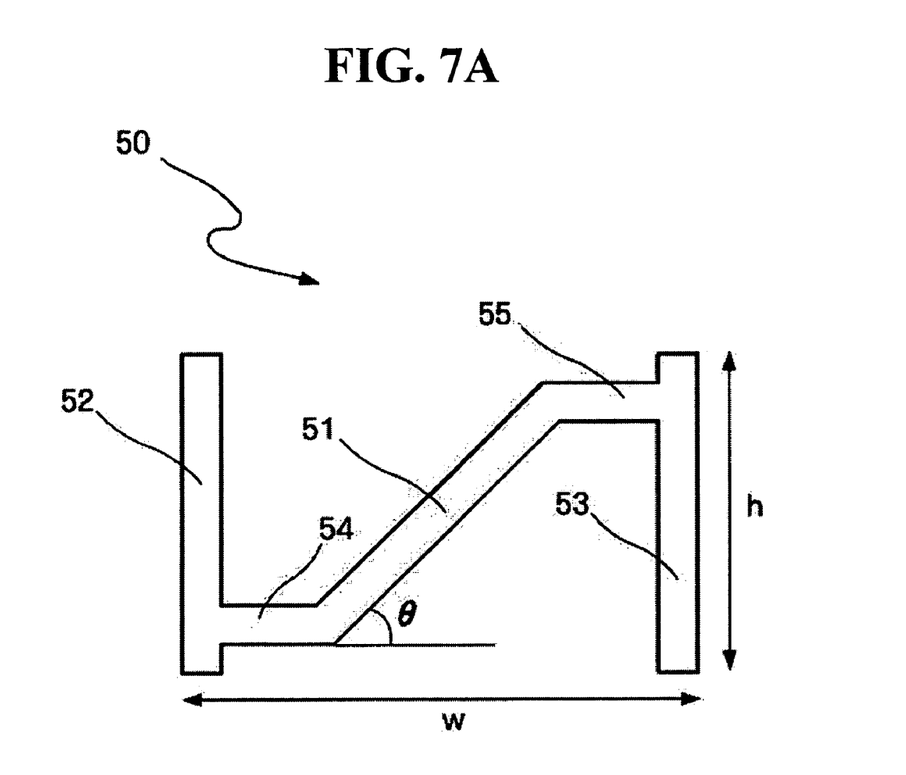
FIGS. 7A through 7D illustrate shapes of a tailed patch according to an embodiment of the present invention.

FIG. 7A illustrates a tailed patch in which an angle θ between a strip unit. In the illustration, θ=4° is considered.

A tailed patch 50 includes a strip unit 51 that is attached at an angle with respect to the axis of a subject such as a rod member and that transfers a torsional wave generated by magnetostriction to the subject, and tail units 52 and 53 that are not attached to the subject but positioned perpendicular to the axis of the subject to concentrate the magnetic flux in the strip unit 51 by absorbing the magnetic flux. The tailed patch 50 may further include connection units 54 and 55 that connect the strip unit 51 with the tail units 52 and 53 and that are formed so as to be parallel with the axis of the subject. The connection units 54 and 55 serve as buffers for preventing the direction of the magnetic flux from being abruptly changed when the magnetic flux absorbed by the tail units 52 and 53 passes through the strip unit 51.

Figure 7B:
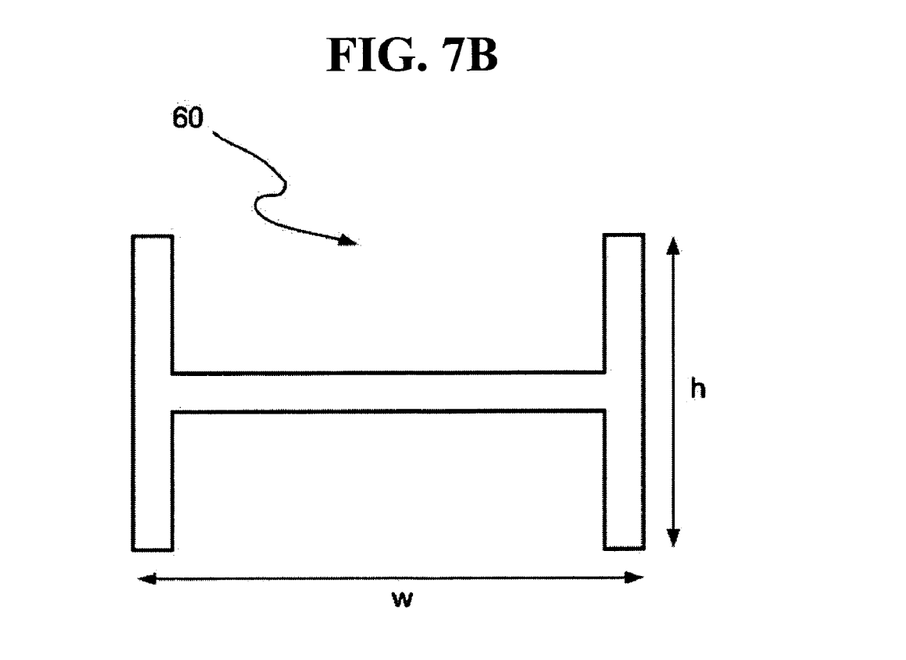
Figure 7C:
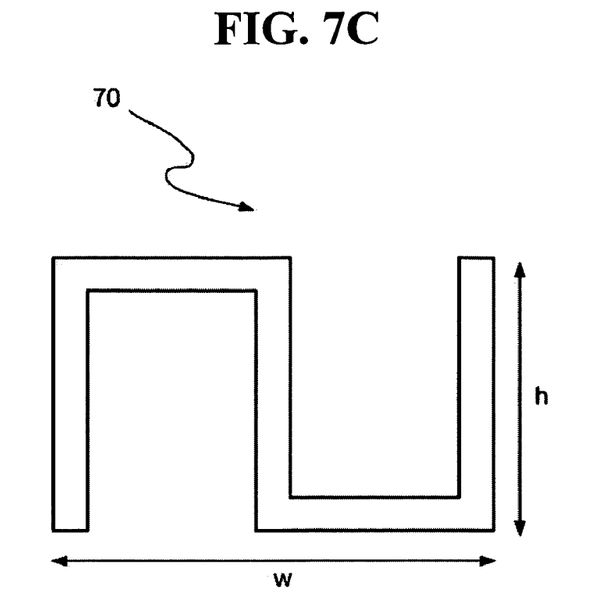
Figure 7D:
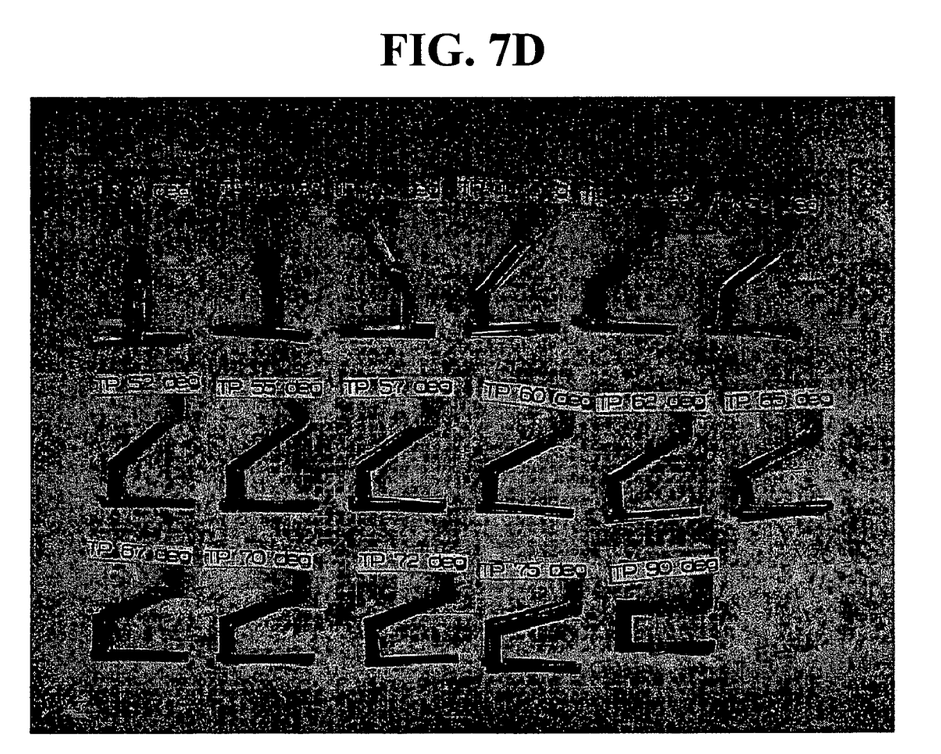

FIG. 7B illustrates a tailed patch 60 when the angle θ shown in FIG. 7A is 0°. FIG. 7C illustrates a tailed patch 70 where the angle θ shown in FIG. 7A is 90°. Since the strip unit 51 is positioned parallel with the axis of the subject in FIG. 7B, the tailed patch 60 is suitable for generation of a longitudinal wave. The tailed patch 70 shown in FIG. 7C is not suitable for generating a torsional wave, but it can be used for another special purpose. Only when the angle θ falls within the range between 0° and 90°, a signal having a large measure in amplitude can be generated. Thus, in the present invention, an experiment is conducted to find the angle θ that generates a torsional wave for each tailed patch 50 having varying the angle θ, as shown in FIG. 7D. It was found that the probability of generating a torsional wave with a large amplitude when the angle θ ranges from 30° to 60°.

Figure 8:
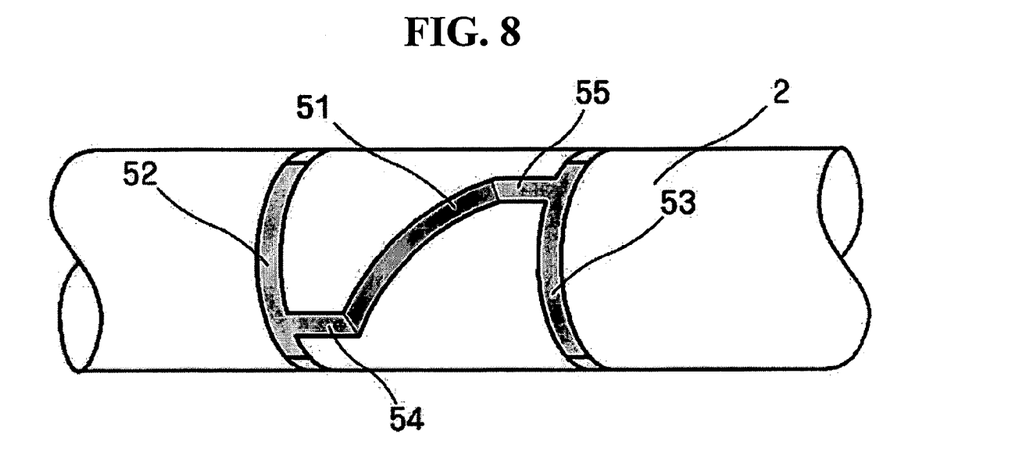
FIG. 8 illustrates a rod to which a tailed patch is attached.

FIG. 8 illustrates the subject 2 to which the tailed patch 50 is attached. Here, the strip unit 51 of the tailed patch 50 should be attached to the surface of the subject 2. However, other portions 52, 53, 54, and 55 do not need to be attached to the subject 2, but should be included inside the first insulator 4.

Here, the strip unit 51 can be attached to the subject 2 using an adhesive such as epoxy resin or by taping the tailed patch 50 on the surface of the subject 2 with a highly adhesive tape several times. To increase the strength of a torsional wave produced with a predetermined input current, a plurality of tailed patches 50 may be attached in the circumferential direction of the subject 2.

Figure 9:
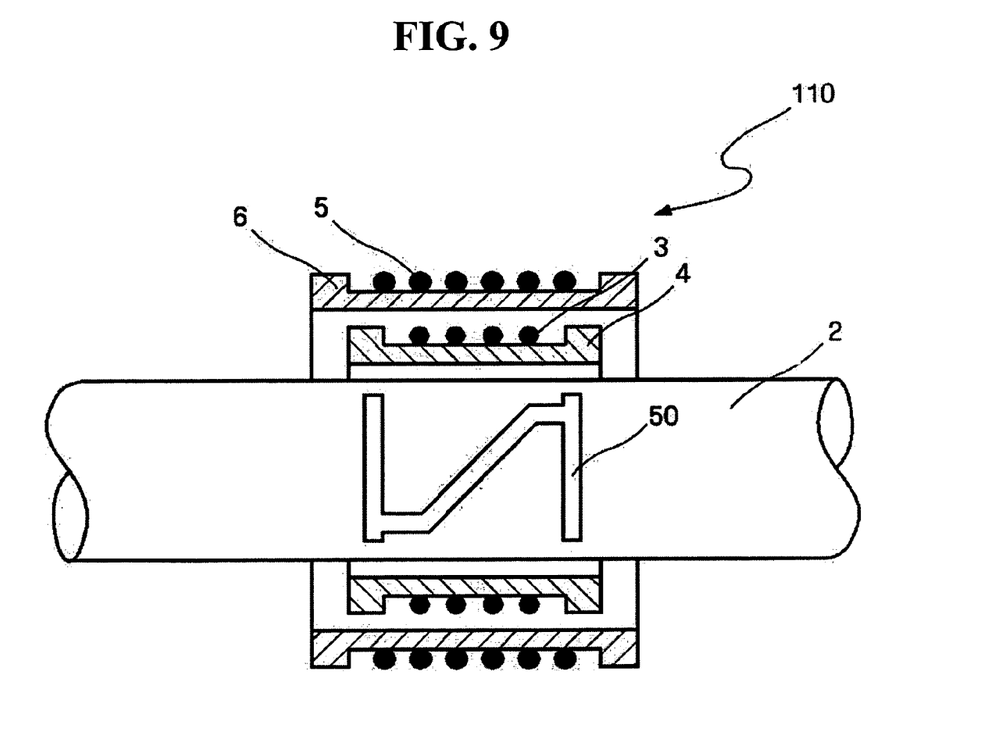
FIG. 9 illustrates the transducer shown in FIG. 6 to which a bias magnetic field is applied.

FIG. 9 illustrates the transducer shown in FIG. 6 to which a bias magnetic field is applied. In the present invention, it is possible to sufficiently excite a subject without a bias magnetic field in order to measure a waveform reflected from a defective area of the subject. That is, the subject is excited by a torsional wave having a higher efficiency than other waves and this magnetic flux is concentrated by the tail units 52 and 53. However, in a case where both more intense excitation and acquisition of a larger amplitude signal are required, the bias magnetic field apparatus as shown in FIG. 9 can be additionally applied to the subject.

To this end, in addition to the structure as shown in FIG. 6, a transducer 110 may further include a second insulator 6 surrounding the driving coil 3 and the first insulator 4 in a manner that it is spaced a predetermined interval apart therefrom, and a bias coil 5 that is wound around the outer circumference of the second insulator 6 and generates a bias magnetic field when a bias current flows.

Figure 10:
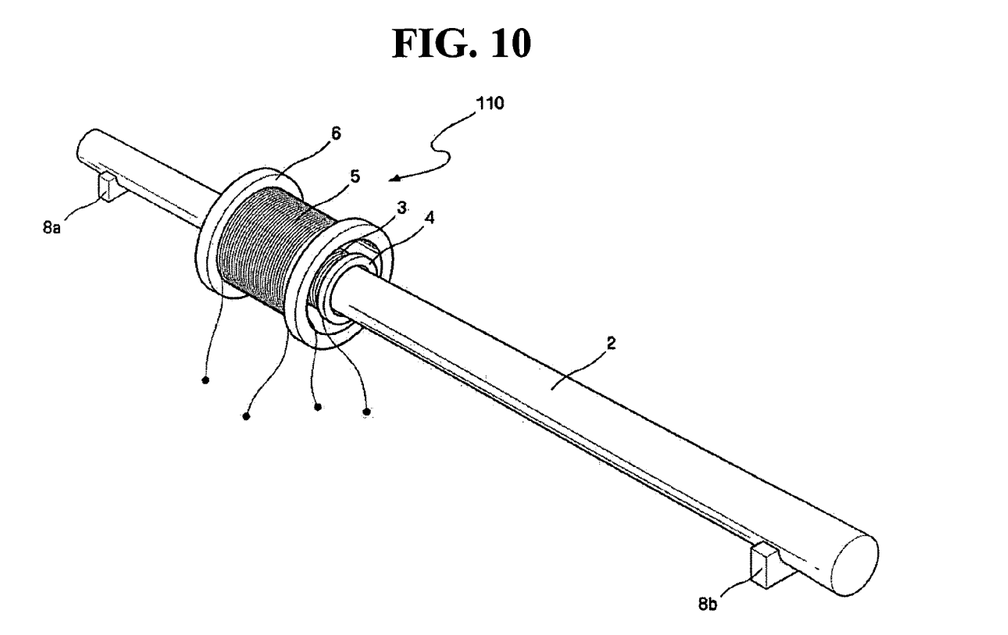
FIG. 10 is a perspective view of FIG. 9.

FIG. 10 is a perspective view of a transducer 110 and the subject 2 according to an embodiment of the present invention. The transducer 110 is installed at a predetermined position on the subject 2, and opposite ends of the subject 2 can be supported by supports 8a and 8b.

To evaluate the performance of the transducer 110 having the tailed patch 50 according to the present invention, several experiments have been conducted. Now, a comparison will be made between Comparative Experimental Example and Experimental Example according to the present invention. In the Comparative Experimental Example, the rectangular patch 9 having a size of 25 mm×2 mm and a shape as shown in FIG. 4 is attached at an angle of 45° with respect to the axis of the subject 2. In the Experimental Example according to the present invention, the tailed patch 50 having the central strip unit 51 that is the same size as the rectangular patch 51 and at an angle θ of 45° is attached to the subject 2.

The rectangular patch 9 and the tailed patch 50 are made of nickel, and the subject 2 is an aluminum pipe having a length of 2 m, an outer diameter of 25 mm, and a thickness of 2 mm. The driving coil 3 is composed of an enamel line having a diameter of 0.3 mm and is wound 280 times around the first insulator 4 having an inner diameter of 26 mm and an outer diameter of 28 mm, and the bias coil 5 composed of an enamel line having a diameter of 0.7 mm is wound 2000 times around the second insulator 5 having an inner diameter of 40 mm and an outer diameter of 50 mm.

Figure 11:
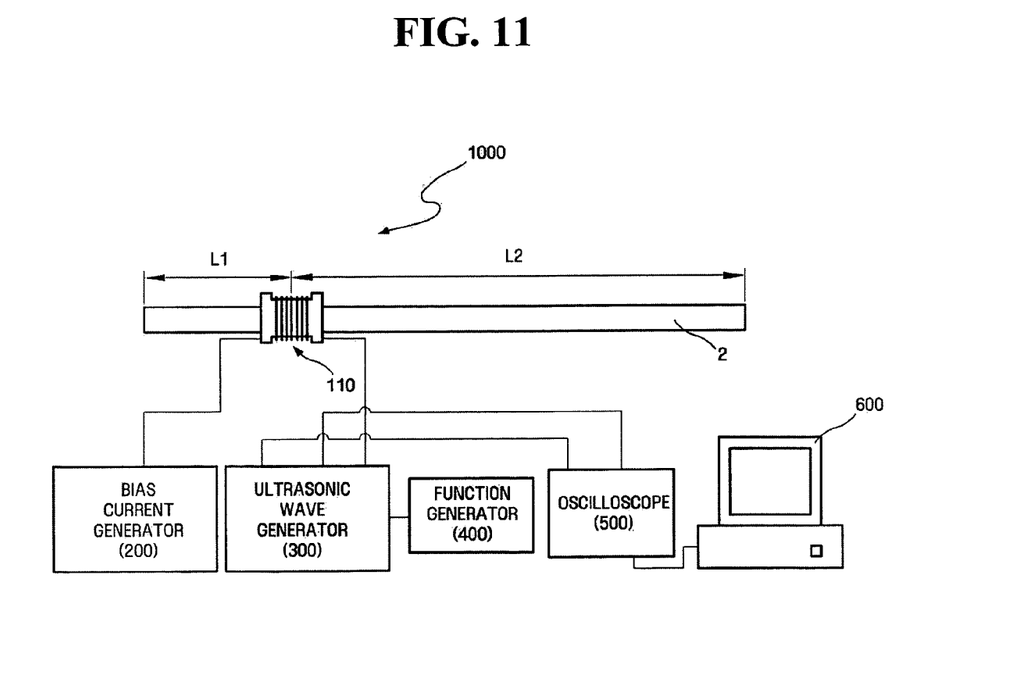
FIG. 11 illustrates the structure of an evaluation apparatus according to an embodiment of the present invention.

FIG. 11 illustrates the structure of an evaluation apparatus 1000 for excitation and measurement of a torsional wave in which various devices, required for conducting experiments on the present invention, are connected to the transducer shown in FIG. 10. When a driving current is input to the driving coil 3, a torsional wave is produced in the subject 2. The input current signal for excitation used is a modulated Gaussian pulse having a peak of 3 ampere and a bias current used is 0.5 ampere. Also, a central frequency of an excitation signal is 72 kHz.

The evaluation apparatus 1000 includes the transducer 110, a bias current generator 200, an ultrasonic wave generator 300, a function generator 400, an oscilloscope 500, and a computer 600.

The function generator 400 generates a waveform desired by a user, and this waveform is input to the ultrasonic wave generator 300.

The ultrasonic wave generator 300 amplifies a driving current of the waveform generated by the function generator 400 and applies the driving current to the transducer 110 to generate a torsional wave. The ultrasonic wave generator 300 also receives and amplifies a voltage signal induced by reflected torsional wave, which is reflected from a defect or an end of the subject 2.

This reflected waveform may be input to the oscilloscope 500 where it can be analyzed. The oscilloscope 500 also allows the user to identify the input waveform.

The computer 600 controls the other electronic devices 200, 300, 400, and 500 according to a user's command, receives a stored signal waveform from the oscilloscope 500, and analyzes the received signal waveform.

The bias current generator 200 can generate a bias magnetic field in the transducer 110 by sending a bias current to the bias coil 5 of the transducer 110. When the bias current is not required as in FIG. 6, the bias current generator 200 may not be provided.

In this embodiment of the present invention, the ultrasonic wave generator 300 is the "RAM-5000" manufactured by Ritec Inc. The RAM-5000 is a general purpose high power ultrasonic wave generator adopting a super heterodyne technique. The main specification of the RMA-5000 is shown below in Table 1.

TABLE 1

| Item | Specification |
| --- | --- |
| Frequency band | 20 KHz-20 MHz |
| Maximum output | 5 kW |
| Normal output impedance | 50 Ω |
| Receiver input impedance | 50 Ω |
| Receiver output impedance | 50 Ω |
| Maximum pulse width | 200 μsec |
| Receiver amplification gain | 20 dB-100 dB |

Figure 12A:
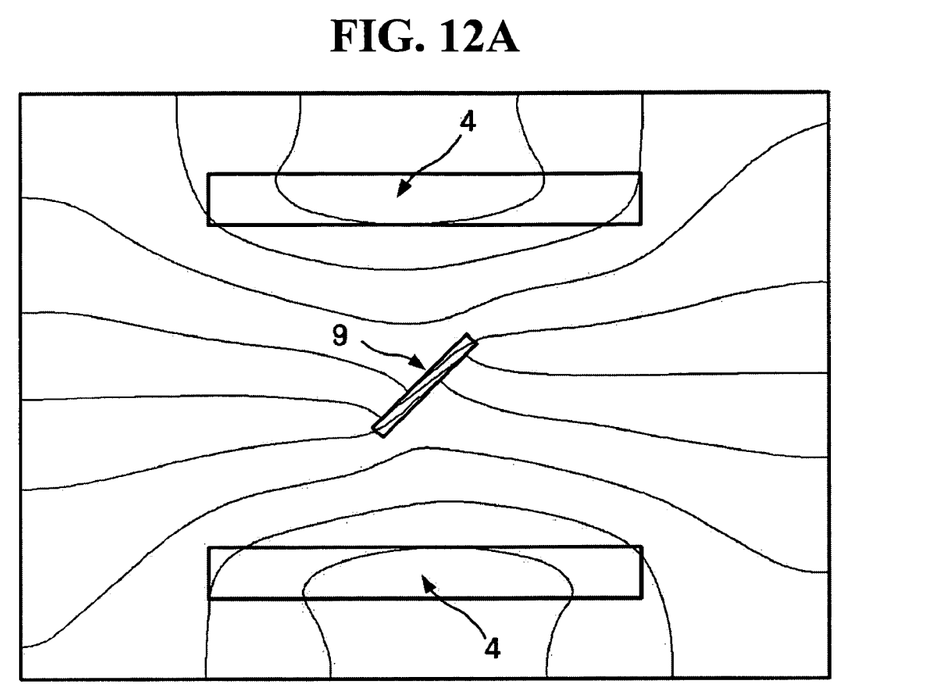
FIG. 12A illustrates a magnetic field formed by a transducer using a rectangular patch.
Figure 12B:
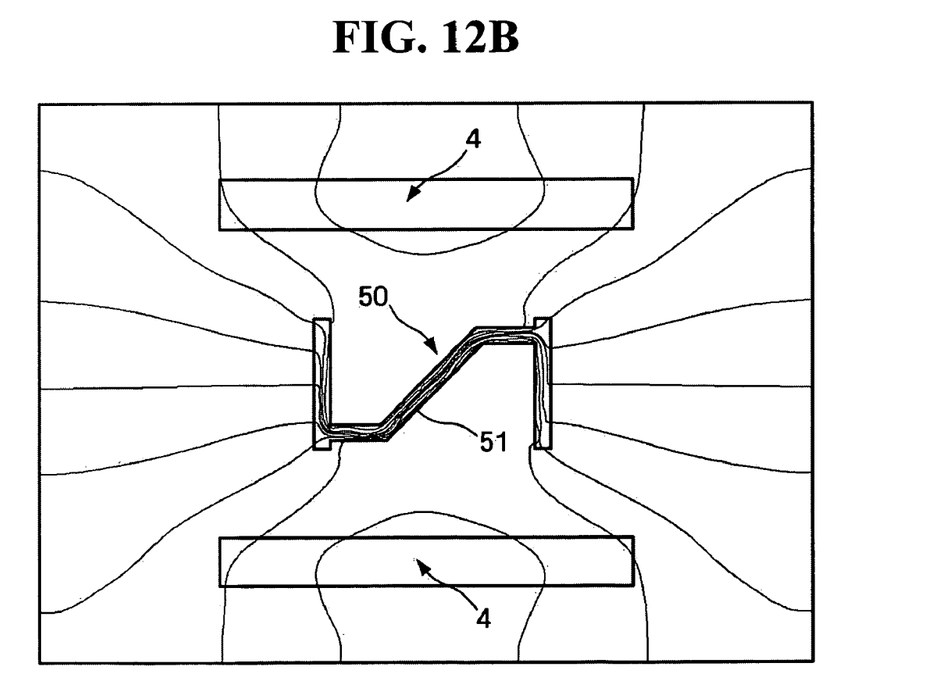
FIG. 12B illustrates a magnetic field formed by a transducer using a tailed patch according to an embodiment of the present invention.

FIG. 12A illustrates a magnetic field formed by a transducer using the rectangular patch 9, and FIG. 12B illustrates a magnetic field formed by a transducer using the tailed patch 50 according to an embodiment of the present invention.

It can be easily seen from a comparison between FIGS. 12A and 12B that a magnetic flux density in the central portion of the tailed patch 50, i.e., the strip unit 51, is higher than in the rectangular patch 9. According to the experiment, the magnetic flux density of the tailed patch 50 is 3.7 times that of the rectangular patch 9. Here, the magnetic flux density of the rectangular patch 9 is 0.04032 Wb/m² and the magnetic flux density in the tailed patch 50 is 0.1506 Wb/m². Thus, it can be concluded that the tailed units 52 and 53 of the tailed patch 50 function to collect a magnetic flux and concentrate the same on the central portion of the tailed patch 50. Since more magnetic flux brings about severer strain to the tailed patch 50 through magnetostriction, it is possible to increase the sensitivity of the transducer, i.e., the amplitude of the produced torsional wave, using the tailed patch 50.

Moreover, it can be seen that the magnetic flux (average direction: 44.75°) flowing through the strip unit 51 shown in FIG. 12B flows in parallel with the strip unit 51 compared to the magnetic flux (average direction: 39.09°) flowing through the rectangular patch 9 shown in FIG. 12A. This is because the tailed patch 50 according to the present invention further includes the tail units 52 and 53 unlike the conventional rectangular patch 9. Such an improvement becomes more distinct when opposite ends of the strip units 51 are connected to the tail units 52 and 53 via connection units 54 and 55 positioned parallel with the axis of the subject 2.

The magnetostriction and inverse magnetostriction used in the present invention can be expressed by:

$$\varepsilon = \frac{\sigma}{E^H} + q*H \quad (1)$$

$$B = \mu^\sigma H + q\sigma$$

where ε indicates a strain, σ indicates a stress applied to a material, $E^H$ indicates an elastic coefficient when a predetermined magnetic field is applied, $\mu_\sigma$ indicates a magnetic permeability when the predetermined stress σ is applied, B indicates a magnetic flux density, and H indicates the magnetic field intensity at an applied magnetic field.

Also, q and q* are coefficients indicating the Villari effect and the Joule effect and are defined by the expressions below.

$$q = \left.\frac{dB}{d\sigma}\right)_H \quad (2)$$

$$q^* = \left.\frac{d\varepsilon}{dH}\right)_\sigma$$

Referring to Equation 1, when a greater magnetic flux density is applied to a patch, a larger strain is generated by magnetostriction. In addition, as the larger stress or strain is generated, the higher magnetic intensity of a magnetic field is induced by inverse magnetostriction. Thus, a larger-amplitude torsional wave can be attained by using the tailed patch 50 shown in FIG. 12B instead of the rectangular patch 9 shown in FIG. 12A, and thus the magnetic intensity of a magnetic field inversely induced by a reflected wave of the torsional wave also increases.

A change in the magnetic field induced by inverse magnetostriction can be easily measured based on a voltage V(t) generated at opposite ends of the driving coil 3, using the Equation:

$$V(t) = -N\frac{d\Phi}{dt} \quad (3)$$

Figure 13A:
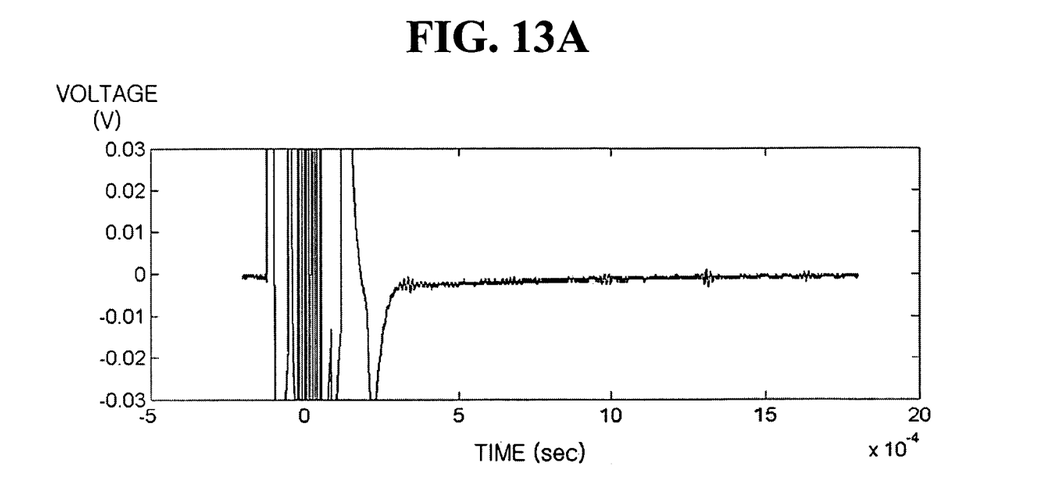
FIG. 13A is a graph showing a signal from the transducer using the rectangular patch.
Figure 13B:
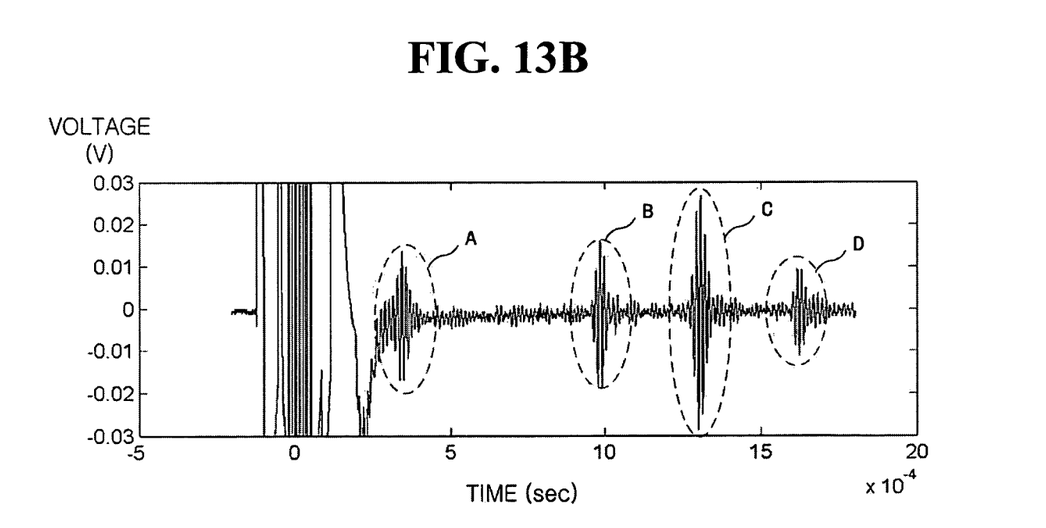
FIG. 13B is a graph showing a signal measured in the transducer using the tailed patch.

FIGS. 13A and 13B are graphs showing voltages V(t) measured in the Comparative Experimental Example and Experimental Example according to the present invention. It can be understood from FIGS. 13A and 13B that there is a large difference between the measured signals.

In FIG. 13B, reference character A denotes a voltage signal of the torsional wave generated in the transducer 110, having traveled a length L1 (shown in FIG. 11) and having been reflected from a first end of the subject 2. Reference character B denotes a voltage signal of the torsional wave generated in the transducer 110, having traveled a length L2 shown in FIG. 11 and having been reflected from a second end of the subject 2. Reference character C denotes a voltage signal of a superposed signal measured in the transducer 110, the superposed signal being obtained by overlapping a signal having been reflected from the first end of the subject 2 and then reflected back from the second end of the subject 2, with a signal having been reflected from the second end of the subject 2 and then reflected back from the first end of the subject 2. Reference character D denotes a voltage signal that has been further reflected from the first end of the subject 2. As such, it is clear that a plurality of signals can be measured through the production of one torsional wave.

Measurement results shown in FIGS. 13A and 13B are summarized in Table 2.

TABLE 2

| | Maximum amplitude (T) of torsional waves | Maximum amplitude (L) of other waves | T/L ratio (SNR) |
|---|---|---|---|
| Tailed patch | 0.0557 | 0.0051 | 10.02 |
| Rectangular patch | 0.00435 | 0.0011 | 3.954 |

Referring to Table 2, the maximum amplitude of torsional waves generated using the tailed patch 50 is about 12.8 times greater than that of other waves generated using the rectangular patch 9. It can be confirmed that measured signal is from torsional waves, by comparing between a theoretical wave velocity and an experimental wave velocity.

Also, if the waves other than the torsional waves are regarded as noise components, a signal-to-noise ratio (SNR) can be calculated by dividing the maximum amplitude of the torsional waves by the maximum amplitude of other waves. When using the tailed patch 50, the signal-to-noise ratio is about 4 times greater than when using the rectangular patch 50.

As is evident from the foregoing experimental results, the transducers 100 and 110 using the tailed patch 50 exhibit an improved sensitivity and SNR compared to the conventional transducer 10 that uses the rectangular patch 9.

The transducers 100 and 110 according to the present invention may be advantageously used to identify the structure of the subject 2 or to detect a defect of the subject 2.

Previously, it has been described that the tail units 52 and 53 of the tailed patch 50 according to the present invention have a straight linear shape and are perpendicular to the axis of the subject 2. In order to know the correlation between the shape of a tail unit and the performance of a transducer, and to discover the optimal shape of the tail unit, simulation of tail units having various shapes was performed.

Figure 14A:
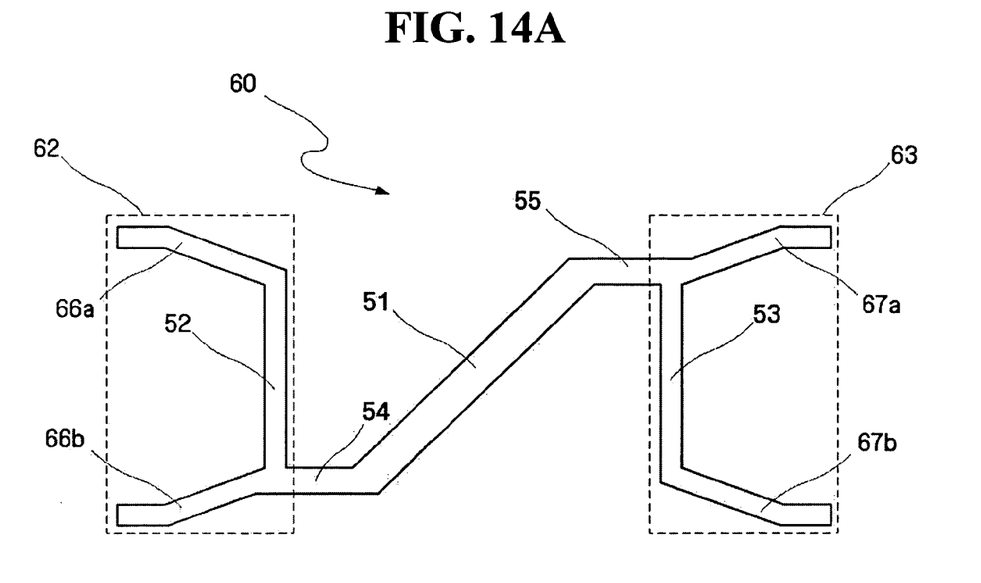
FIG. 14A illustrates the shape of a tailed patch according to another embodiment of the present invention.
Figure 15A:
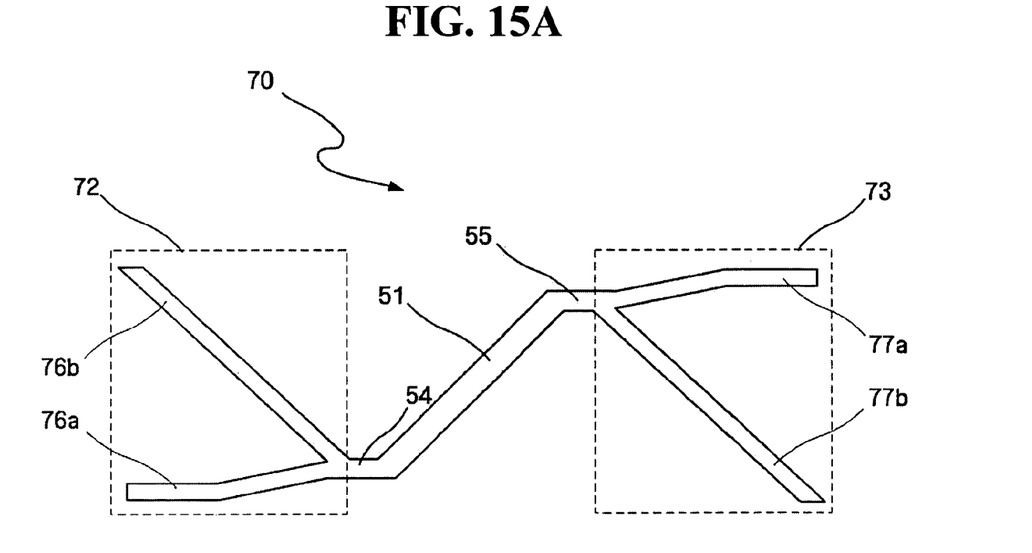
FIG. 15A illustrates the shape of a tailed patch according to still another embodiment of the present invention.
Figure 15B:
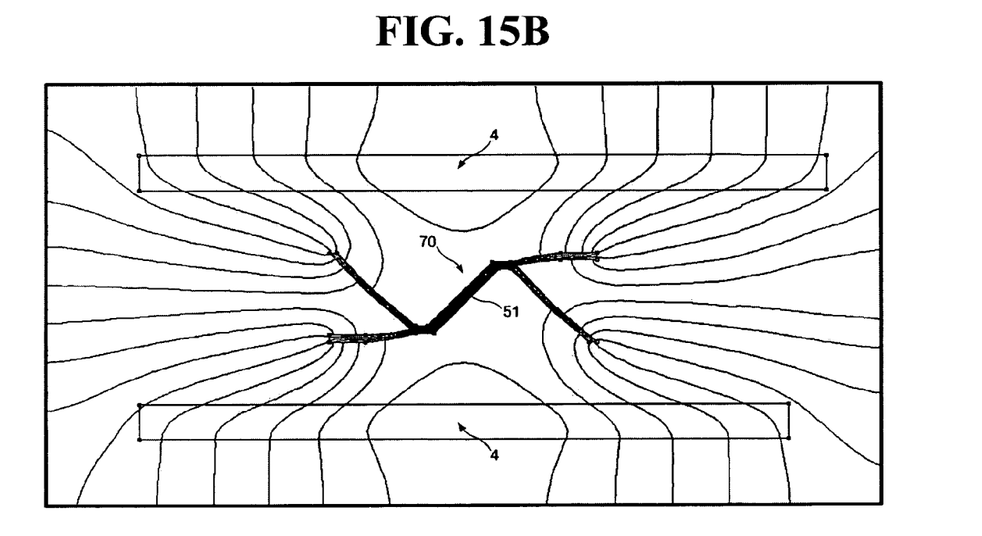
FIG. 15B illustrates a magnetic field formed by a transducer using the tailed patch shown in FIG. 15A.
Figure 16A:
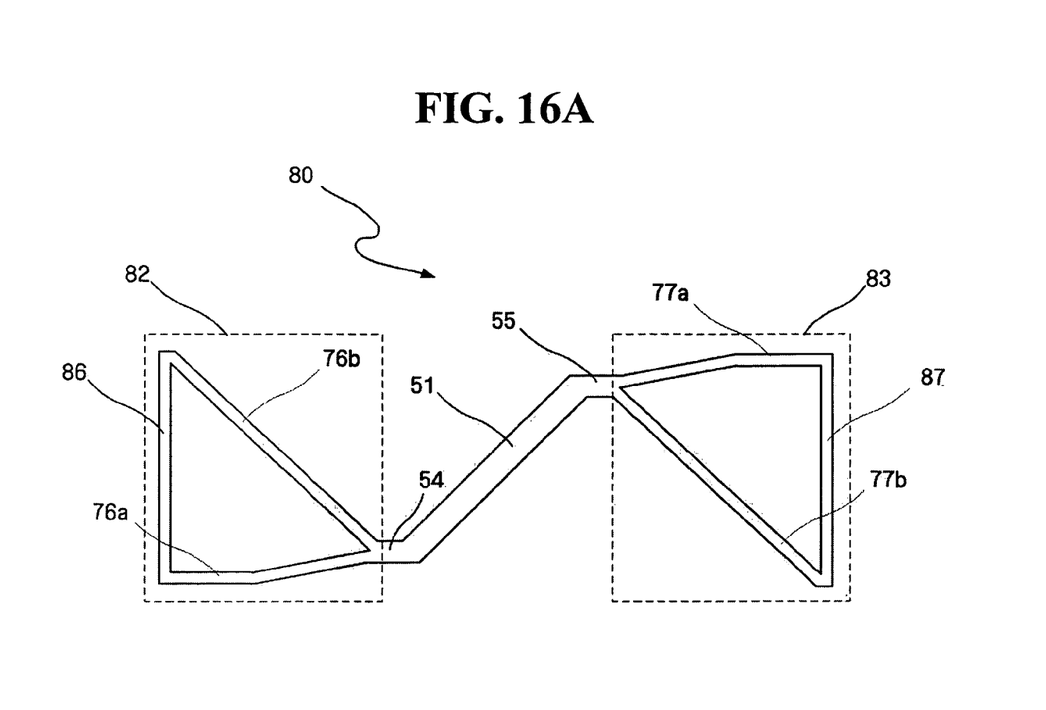
FIG. 16A illustrates the form of a tailed patch according to yet another embodiment of the present invention.
Figure 16B:
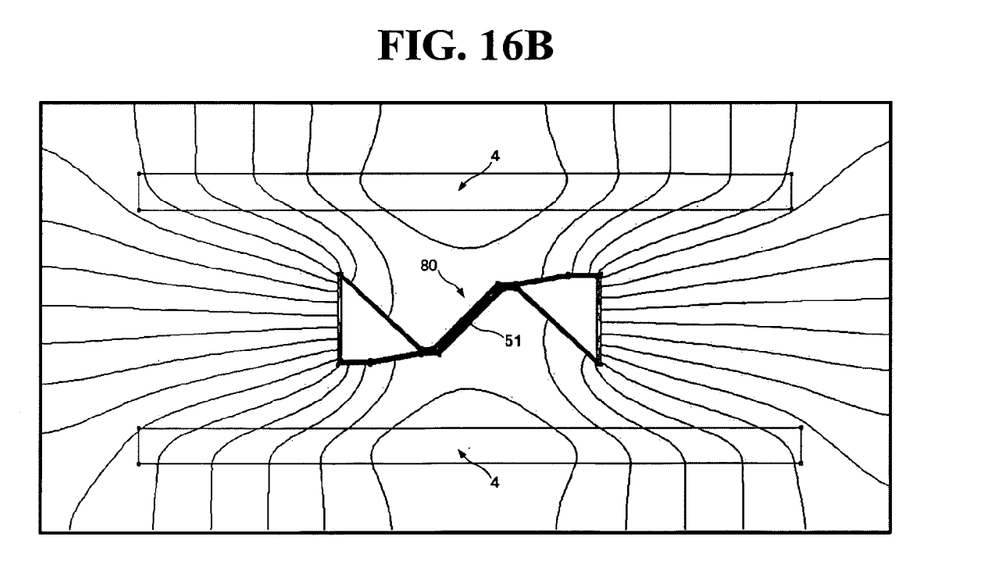
FIG. 16B illustrates a magnetic field formed by a transducer using the tailed patch shown in FIG. 16A.

One restriction for simulations is to maintain the same amount of materials in the tail units. The simulation results reveal three optimal shapes of the tail units having superior performance, which are shown in FIGS. 14A, 15A, and 16A. The magnetic fields formed around these respective tailed patches are shown in FIGS. 14B, 15B, and 16B.

First, a tailed patch 60 according to an embodiment shown in FIG. 14A includes branches 66a/66b and 67a/67b at opposite ends of each of the rectangular tail units 52 and 53 of the N-type tailed patch 50, respectively. The branches 66a/66b and 67a/67b are arranged in a direction substantially perpendicular to the axis of the rectangular tail units 52 and 53, but slightly flared to their ends of the tailed patch 60.

Figure 14B:
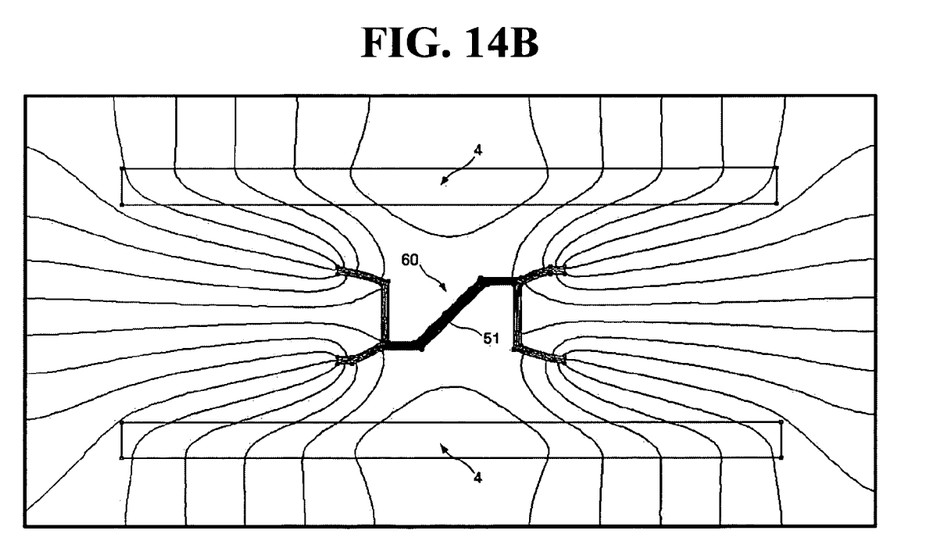
FIG. 14B illustrates a magnetic field formed by a transducer using the tailed patch shown in FIG. 14A.

FIG. 14B illustrates a magnetic field formed by a transducer using the tailed patch 60. In this case, an average magnetic flux density formed in a strip unit 51 is 0.820 Wb/m$^2$, which is 20% higher than that of the N-type tailed patch 50.

Tail units 72 and 73 of a tailed patch 70 according to an embodiment shown in FIG. 15A include first branches 76a and 77a substantially parallel with the axis of the subject, and second branches 76b and 77b substantially perpendicular to a strip unit 51 of the tailed patch 70.

FIG. 15B illustrates a magnetic field formed by a transducer using the tailed patch 70. In this case, the average magnetic flux density formed in the strip unit 51 of the tailed patch 70 is 0.914 Wb/m$^2$, which is 34% higher than that of the N-type tailed patch 50.

Tail units 82 and 83 of a tailed patch 80 according to an embodiment shown in FIG. 16A further include branch connection units 86 and 87 that connect ends of the first branches 76a and 77a and ends of the second branches 76b and 77b. The branch connection units 86 and 87 are formed perpendicular to the axis of the subject.

FIG. 16B illustrates a magnetic field formed by a transducer using the tailed patch 80. In this case, the average magnetic flux density formed in the strip unit 51 of the tailed patch 80 is 0.899 Wb/m$^2$, which is 32% higher than that of the N-type tailed patch 50. On the assumption that the same amount of material is used when compared with the embodiment shown in FIG. 15B, magnetic flux concentration is not significantly affected by the branch connection units 86 and 87 shown in 16B.

When a torsional wave is produced by the transducer 100, 110 using the tailed patch 50, 60, 70, or 80 according to the illustrative embodiments of the present invention, a method for suppressing vibration (e.g., damping) can be optionally added for the purpose of preventing vibration of tail units that occur at a specific frequency.

According to the present invention, both the sensitivity and the signal-to-noise ratio of a magnetostrictive transducer can be improved. In addition, use of the magnetostrictive transducer according to the present invention allows a torsional wave generated therefrom to be efficiently used in identifying the structure of a subject.

In conclusion, those skilled in the art will appreciate that many variations and modifications can be made to the preferred embodiments without substantially departing from the principles of the present invention. Therefore, the disclosed preferred embodiments of the invention are used in a generic and descriptive sense only and not for purposes of limitation.

What is claimed is:

1. A magnetostrictive transducer having a ferromagnetic patch that attaches to a predetermined position of a subject, a cylindrical insulator installed around the periphery of the ferromagnetic patch, and a coil wound around the cylindrical surface of the insulator, wherein the ferromagnetic patch comprises:

a strip unit attached to the subject in an inclined manner with respect to an axis of the subject and transferring the torsional wave to the subject; and tail units formed at opposite ends of the strip unit and concentrating a magnetic flux on the strip unit when current is applied to the coil, wherein the ferromagnetic patch generates a torsional wave based on a magnetostrictive effect in the subject when current is applied to the coil, and wherein the ferromagnetic patch further comprises a connection unit that is connected to the strip unit and the tail unit and is formed in a direction parallel with the axis of the subject.

2. The magnetostrictive transducer of claim 1, wherein each of the tail units comprises a rectangular portion that is perpendicular to the axis of the subject.

3. The magnetostrictive transducer of claim 1, wherein each of the tail units comprises a rectangular portion perpendicular to the axis of the subject and branches extending from opposite ends of the rectangular portion, wherein the branches are substantially parallel with the axis of the subject.

4. The magnetostrictive transducer of claim 1, wherein each tail unit comprises a first branch substantially parallel with the axis of the subject and a second branch substantially perpendicular to the strip unit.

5. The magnetostrictive transducer of claim 1, wherein each tail unit comprises a first branch substantially parallel with the axis of the subject, a second branch substantially perpendicular to the strip unit, and a branch connection unit that connects ends of the first and second branches.

6. The magnetostrictive transducer of claim 1, wherein the strip unit is attached to the subject at a predetermined angle with respect to the axis of the subject.

7. The magnetostrictive transducer of claim 1, further comprising:
   an external insulator that surrounds the coil and the insulator in a manner that it is spaced a predetermined interval apart therefrom; and
   a bias coil that is wound around the outer surface of the external insulator.

8. The magnetostrictive transducer of claim 1, wherein a plurality of ferromagnetic patches are attached to the subject and spaced a predetermined interval apart from each other in the circumferential direction of the subject.

9. The magnetostrictive transducer of claim 1, wherein the subject is a rod member having a predetermined length.

* * * * *